(12) United States Patent
Don Michael

(10) Patent No.: US 6,216,816 B1
(45) Date of Patent: Apr. 17, 2001

(54) STETHOSCOPE HAVING TWO INPUT DEVICES

(76) Inventor: T. Anthony Don Michael, 4109 Sill Pl., Bakersfield, CA (US) 93306

( * ) Notice: Subject to any disclaimer, the term of this patent is extended or adjusted under 35 U.S.C. 154(b) by 0 days.

(21) Appl. No.: 09/461,220

(22) Filed: Dec. 16, 1999

(51) Int. Cl.[7] .................................................. A61B 7/02
(52) U.S. Cl. ........................................ 181/131; 181/137
(58) Field of Search .................................. 181/131, 137; 381/67

(56) References Cited

U.S. PATENT DOCUMENTS 4,239,089 * 12/1980 Nelson .................................. 181/131
5,861,584 * 1/1999 Shieh .................................... 181/131

* cited by examiner

Primary Examiner—Khanh Dang
(74) Attorney, Agent, or Firm—Browdy and Neimark

(57) ABSTRACT

A stethoscope having a chest-piece which is composed of a base member fixed to flexible tubes, a pickup mounting member rotatable about a first axis relative to the base member, and a plurality of pickups carried by the pickup mounting member. The plurality of pickups consist of one diaphragm and one bell; the diaphragm and the bell extend in diametrically opposite directions perpendicular to the first axis and extend along a common axis of symmetry; the bell has an outer end which lies in a first plane remote from the first axis, an inner end between the outer end and the first axis and a curved wall between the outer and inner ends; and the outer end has an external diameter less than 30 mm.

7 Claims, 1 Drawing Sheet

STETHOSCOPE HAVING TWO INPUT DEVICES

BACKGROUND OF THE INVENTION

The present invention relates to stethoscopes, and particularly stethoscopes having a plurality of input devices.

A stethoscope is a primary diagnostic tool utilized by physicians and is composed essentially of two ear pieces, an input unit, commonly known as a chest-piece, and two flexible hollow tubes which connect the chest-piece to the ear pieces. The tubes constitute, essentially, acoustic wave guides that confine acoustic pressure waves and transmit these waves from the chest-piece to the ear pieces.

The chest-piece of a stethoscope may be constituted by a single input device, or sound pickup, or by a plurality of such devices. When a plurality of devices are provided, the chest-piece will be composed of a coupler, or support, member connected to the flexible tubes and a turret which carries the sound pickups. The turret is rotatable to bring a selected pickup into a position for use, in which that pickup is in acoustic communication with the flexible tubes.

There are two basic types of pickup: those which are provided with a diaphragm; and those which are commonly referred to as bells. In the type provided with a diaphragm, the diaphragm is placed in contact with a region of the patient's body. Vibrations at the surface of the body are conveyed to the diaphragm and from there to an air space in communication with the diaphragm. The acoustic vibrations induced in the air space are then transmitted to the ear pieces via the hollow tubes. The pickups of the bell type have, as the name implies, a bell shape which is open at both ends. The larger diameter end of the bell is intended to be placed in contact with the patient's body, while the smaller diameter end is provided with an opening which communicates with the flexible tubes. Each type of pickup is suited to be used on certain parts of a patient's body to detect certain types of body sounds.

Known chest-pieces provided with a plurality of pickups include: chest-pieces provided with three pickups angularly offset from one another by 120° about an axis of rotation of the turret on which the pickups are mounted, as shown, for example, in FIG. 4; chest-pieces having two pickups, one aligned with the longitudinal axis of the chest-piece and one oriented perpendicular to that longitudinal axis; and chest-pieces having two pickups spaced 180° apart about the longitudinal axis of the turret, as shown, for example, in FIG. 5.

In the case of known chest-pieces of the first-mentioned type, one of the pickups is a bell having a relatively small maximum diameter and a relatively high ratio of depth to maximum diameter. This bell is well suited for monitoring heart sounds because it is able to fit completely between two adjacent ribs of an average patient and can thus be positioned so that the transmission of sounds to the bell is not obstructed by a rib. Known chest-pieces of the second- and third-mentioned types do not include the a bell having the form described above, but rather a comparatively larger diameter element which functions in the manner of a bell but which is too large to fit completely between the ribs of an average adult patient.

When a diaphragm type pickup is to be employed for listening to body sounds, sound detection can frequently be improved if the pickup is applied to a body surface with a firm, steady pressure. It is difficult for a user to apply such pressure with the known stethoscopes, either because there is no suitable pressure-applying surface located diametrically opposite the diaphragm, as in the prior art device shown in FIG. 4, or because the pickup located diametrically opposite the diaphragm has a shape which does not allow accurate and comfortable positioning of the user's finger to produce the requisite firm and steady pressure, as in the prior art device shown in FIG. 5.

BRIEF SUMMARY OF THE INVENTION

It is a primary object of the present invention to facilitate the use of a stethoscope having a plurality of pickups, one of which is a diaphragm.

A more specific object of the invention is to enable the diaphragm-type pickup of a stethoscope to be easily applied with a firm and steady pressure against a patient's body.

Yet another object of the invention is to achieve the above results while providing a bell-type pickup that is well suited for monitoring heart sounds.

The above and other objects are achieved, according to the present invention, in a stethoscope having a chest-piece which is composed of a base member fixed to flexible tubes, a pickup mounting member rotatable about a first axis relative to the base member, and a plurality of pickups carried by the pickup mounting member, by the improvement wherein: the plurality of pickups consist of one diaphragm and one bell; the diaphragm and the bell extend in diametrically opposite directions perpendicular to the first axis and extend along a common axis of symmetry; the bell has an outer end which lies in a first plane remote from the first axis, an inner end between the outer end and the first axis and a curved wall between the outer and inner ends; and the outer end of the bell has an external diameter less than 3 cm.

When a chest-piece is provided with two pickups having the form and relative locations described above, the bell is well suited for detecting heart sounds because it is dimensioned to fit between two adjacent ribs, and the bell is also well adapted to act as a receptacle for a finger of a user who wishes to listen to body sounds with the aid of the diaphragm and who wishes to push the diaphragm firmly against the patient's body.

DETAILED DESCRIPTION OF THE INVENTION

Figure 1:
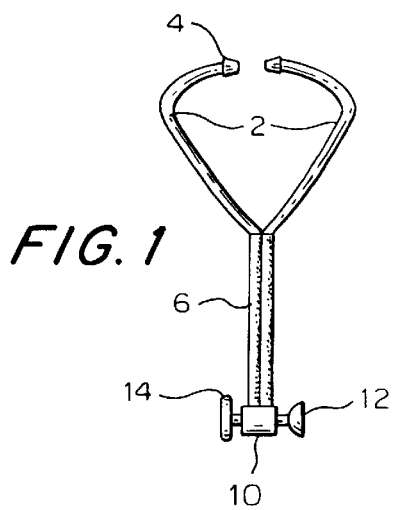
FIG. 1 is a simplified pictorial view of a stethoscope equipped with a chest-piece according to the invention.

FIG. 1 is a pictorial view which shows the basic arrangement of a conventional stethoscope. This is constituted by curved, hollow metal tubes 2 connected at one end to ear pieces 4 and at the other end to flexible, hollow tubes 6, which are usually made of rubber. Tubes 6 extend between tubes 2 and a chest-piece 10. Components 2, 4 and 6 are conventional in the art.

According to the present invention, chest-piece 10 is provided with two pickups, constituted by a metal bell 12 and a diaphragm 14.

Figure 2:
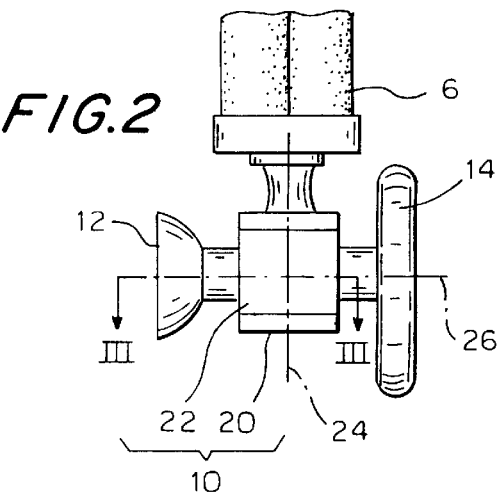
FIG. 2 is a detail view of the chest-piece portion of the stethoscope of FIG. 1.

Chest-piece 10 is shown in greater detail in FIG. 2 and is composed essentially of a base, or support, member 20 and a turret 22. Turret 22 is rotatable about an axis 24, which is the longitudinal axis of chest-piece 10, and carries bell 12 and diaphragm 14. Bell 12 and diaphragm 14 are both centered on, i.e., axially symmetrical relative to, a common axis 26 that is perpendicular to axis 24. Thus, with respect to turret 22, bell 12 and diaphragm 14 are diametrically opposite one another.

Figure 3:
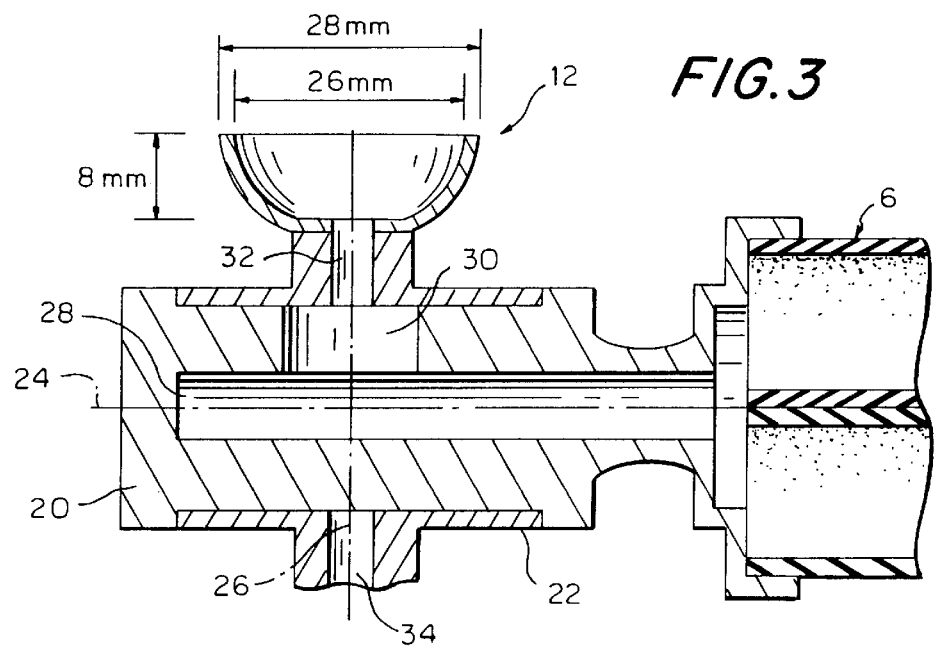
FIG. 3 is a cross-sectional view taken along the line III—III of FIG. 2.

FIG. 3 is a cross-sectional view showing a part of chest-piece 10 in greater detail. As is already known in the art, member 20 has a hollow interior composed of a circularly cylindrical longitudinal passage 28 and a circularly cylindrical laterally extending passage 30. Passage 28 extends along longitudinal axis 24 and is closed at one end and open at the opposite end to communicate with the interior of tubes 6. Passage 30 extends perpendicular to axis 24.

Turret 22 is rotatable about axis 24 relative to member 20 to bring axis 26 into alignment with the axis of passage 30 so that either a passage 32 associated with bell 12 or a passage 34 associated with diaphragm 14 is in communication, and aligned, with passage 30. When turret 22 is in the described position relative to passage 30, acoustic energy from either bell 12 or diaphragm 14 will be transmitted to the interior of tubes 6 via laterally extending passage 30 and longitudinal passage 28. In FIG. 3, the passage in bell 12 is in such a position.

Member 20 and passages 28 and 30 may have the form and dimensions of a similar member of the chest-piece of a commercially available stethoscope marketed by Hewlett Packard under the model designation Rappaport Sprague.

Preferred significant dimensions for bell 12 are also shown in FIG. 3. Bell 12 is preferably a metal member having the form of a portion of a sphere with a radius of curvature of about 14–15 mm. The outer end of bell 12, which will be in contact with a patient's skin, preferably has an external diameter of less than 30 mm, the diameter being 28 mm in the illustrated embodiment, and a depth between the inner and outer ends of about 8 mm.

Both the shape and dimensions of bell 12 are beneficial because, as noted above, they enable bell 12, when it is the active pickup device, to be positioned between two ribs of a patient so that the ribs do not interfere with the transmission of heart sounds or other body sounds to bell 12. On the other hand, when diaphragm 14 is in the active position, the shape and dimensions of bell 12 are such that it provides a convenient and comfortable receptacle for the user's finger to allow the user to apply a firm and steady pressure which acts to press diaphragm 14 against the patient's body, to thereby improve the quality of the sounds delivered to ear pieces 4.

Figure 4:
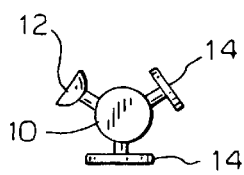
FIGS. 4 and 5 are end views of two chest-pieces according to the prior art.
Figure 5:
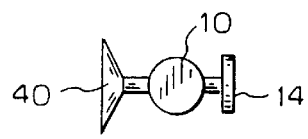

In contrast, the prior art chest-piece shown in FIG. 4 does not have a convenient and comfortable receptacle for the user's finger to allow the user to apply a firm and steady pressure which acts to press either diaphragm 14 against the patient's body, and the pickup device 40 of the prior art device shown in FIG. 5 is relatively wide and shallow, having a maximum diameter of the order of 35 mm at the end which is intended to come in contact with a patient's body, and a depth, between the inner and outer ends thereof, of substantially 6 mm. In addition, the outer portion of pickup device 40 is made of a hard plastic material.

While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein.

What is claimed is:

1. In a stethoscope having a chest-piece which is comprised of a base member fixed to flexible tubes, a mounting member rotatable about a first axis relative to the base member and a plurality of pickups carried by the mounting member, the improvement wherein: said plurality of pickups consist of one diaphragm and one bell; said diaphragm and said bell extend in diametrically opposite directions perpendicular to the first axis and extend along a common axis of symmetry; said bell has an outer end which lies in a first plane remote from said first axis, an inner end between said outer end and said first axis and a curved wall between said outer and inner ends, and said outer end has an external diameter less than 30 mm.

2. The stethoscope of claim 1 wherein said outer end has an external diameter of substantially 28 mm.

3. The stethoscope of claim 2 wherein said bell has a depth, between said inner and outer ends, of substantially 8 mm.

4. The stethoscope of claim 3 wherein said curved wall has a radius of curvature of substantially 14.3 mm.

5. The stethoscope of claim 2 wherein said curved wall has a radius of curvature of substantially 14.3 mm.

6. The stethoscope of claim 1 wherein said curved wall has a radius of curvature of substantially 14.3 mm.

7. The stethoscope of claim 1 wherein said bell has a depth, between said inner and outer ends, of substantially 8 mm.

* * * * *